United States Patent [19]

Bottelberghe

[11] Patent Number: 4,924,018

[45] Date of Patent: May 8, 1990

[54] ALKYLALUMINOXANE PROCESS

[75] Inventor: Scott A. Bottelberghe, Port Allen, La.

[73] Assignee: Ethyl Corporation, Richmond, Va.

[21] Appl. No.: 371,192

[22] Filed: Jun. 26, 1989

[51] Int. Cl.$^5$ .............................................. C07F 5/06
[52] U.S. Cl. ................................................... 556/179
[58] Field of Search ......................................... 556/179

[56] References Cited

U.S. PATENT DOCUMENTS

| | | | |
|---|---|---|---|
| 2,744,074 | 5/1956 | Theobald | 556/179 X |
| 3,184,490 | 5/1965 | Davison | 556/179 X |
| 3,220,797 | 11/1965 | Lester | 556/179 X |
| 3,242,099 | 3/1966 | Manyik et al. | 252/429 |
| 3,300,458 | 1/1967 | Manyik et al. | 260/88.2 |
| 3,454,615 | 7/1969 | Tani et al. | 556/179 |
| 3,655,329 | 4/1972 | Shih et al. | 556/179 X |
| 4,544,762 | 10/1985 | Kaminsky et al. | 556/179 |
| 4,665,208 | 5/1987 | Welborn, Jr. et al. | 556/179 |
| 4,730,071 | 3/1988 | Schoenthal et al. | 556/179 |
| 4,730,072 | 3/1988 | Schoenthal et al. | 556/179 |
| 4,772,736 | 9/1988 | Edwards et al. | 556/179 |

FOREIGN PATENT DOCUMENTS

| | | | |
|---|---|---|---|
| 0279586 | 8/1988 | European Pat. Off. | 556/179 |
| 0158792 | 9/1982 | Japan | 556/179 |
| 102562 | of 0000 | Poland | 556/179 |

*Primary Examiner*—Paul F. Shaver
*Attorney, Agent, or Firm*—Joseph D. Odenweller

[57] ABSTRACT

Alkylaluminoxanes are made in a continuous process by feeding an inert solvent solution of an alkyl aluminum compound and a water/inert solvent emulsion to a first reaction vessel maintained at about −20° to 30° C. and transferring reaction mixture to a second reaction zone at a rate which maintains a constant liquid level in the first reaction vessel and results in an average residence time of about 1-60 minutes.

18 Claims, 1 Drawing Sheet

U.S. Patent    May 8, 1990    4,924,018
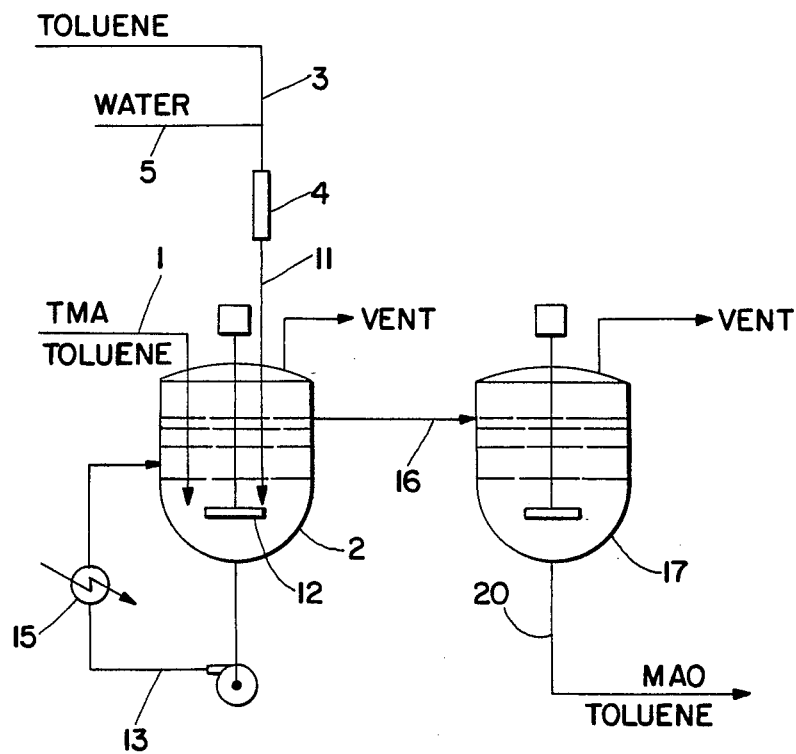

4,924,018

ALKYLALUMINOXANE PROCESS

BACKGROUND

Vandenberg, U.S. Pat. No. 3,219,591, reported the catalytic activity of compounds formed by the reaction of trialkyl aluminum with limited amounts of water in the polymerization of epichlorohydrin and other oxiranes. Shortly thereafter Manyik et al., U.S. Pat. No. 3,242,099, reported the use of aluminoxanes, made by reacting 0.85-1.05 moles of water with hydrocarbyl aluminum compounds such as triisobutyl aluminum, as co-catalysts with certain transition metal compounds in the polymerization of mono-unsaturate α-olefins; e.g. ethylene, propylene. Isobutylaluminoxane was made by adding an equal mole quantity of water to a heptane solution of triisobutyl aluminum.

Manyik et al. U.S. Pat. No. 3,300,458 prepare alkylaluminoxane by passing a hydrocarbon through water to form a wet hydrocarbon and mixing the wet hydrocarbon and an alkyl aluminum/hydrocarbon solution in a conduit.

Sinn et al. U.S. Pat. No. 4,404,344 prepare methylaluminoxane by adding trimethyl aluminum to a slurry of $CuSO_4.5H_2O$ in toluene. Water as a metal hydrate controls its reactivity with the trimethyl aluminum. Kaminsky et al. U.S. Pat. No. 4,544,762 is similar except it uses an aluminum salt hydrate to supply the water. Likewise Welborn et al. U.S. Pat. No. 4,665,208 describe the use of other metal salt hydrates such as $FeSO_4.7H_2O$ as a water source in preparing aluminoxane.

Schoenthal et al. U.S. Pat. No. 4,730,071 show the preparation of methylaluminoxane by dispersing water in toluene using an ultrasonic bath to cause the dispersion and then adding a toluene solution of trimethyl aluminum to the dispersion. Sohoenthal et al. U.S. Pat No. 4,730,072 is similar except it uses a high speed, high shear-inducing impeller to form the water dispersion.

Edwards et al. U.S. Pat. No. 4,772,736 describe an aluminoxane process in which water is introduced below the surface of a solution of hydrocarbyl aluminum adjacent to a stirrer which serves to immediately disperse the water in the hydrocarbon solution.

Pasynkiewiez et al., Pol. No. 102,562, discloses a continuous process for making alkylaluminoxanes and caution that the reaction mixture must be removed from the reaction zone within 1-10 seconds.

SUMMARY

Alkylaluminoxanes are made in a continuous process by feeding (1) an inert solvent (e.g. toluene) solution of an alkyl aluminum compound (e.g. trimethyl aluminum) and (2) an inert solvent/water emulsion to a first reaction vessel at about −20° C. to 30° C. and transferring reaction mixture from the first reaction vessel to a second reaction vessel to maintain a constant liquid level in the first reaction vessel and provide an average residence time of 1-60 minutes.

DESCRIPTION OF THE DRAWING

The drawing is a schematic flow diagram of the process of the invention.

DESCRIPTION OF THE PREFERRED EMBODIMENTS

A preferred embodiment of the invention is a continuous process for making an alkylaluminoxane, said process comprising:
(A) feeding a solution of an alkyl aluminum compound in an inert solvent to a first reaction zone,
(B) forming an emulsion of water in an inert solvent and feeding said emulsion to said first reaction zone, the ratio of moles of water to aluminum atoms being about 0.4-1:1,
(C) removing reaction mixture from said first reaction zone at a rate that maintains a constant liquid volume in said first reaction zone,
further characterized in that the combined feed rate of said solution of an alkyl aluminum compound and said emulsion results in an average residence time in said first reaction zone of about 1-60 minutes.

Any aluminum compound capable of reacting with water to form an aluminoxane can be used. This includes trialkyl aluminums, triaryl aluminums, mixed alkyl aryl aluminums, alkyl aluminum dihalides, dialkyl aluminum halides, alkylaluminum sesquihalides, dialkyl aluminum alkoxides and the like.

The preferred aluminum compounds are the hydrocarbyl aluminum compounds, especially trialkyl aluminum compounds such as trimethyl aluminum, triethyl aluminum, triisobutyl aluminum, tri-n-hexyl aluminum, tri-octyl aluminum and the like. Of these the more preferred are the tri-$C_{l-4}$-alkylaluminum compounds such as trimethyl aluminum, triethyl aluminum and triisobutyl aluminum.

Of the various hydrocarbyl aluminoxanes, the more difficult to prepare are methylaluminoxane and ethylaluminoxane because of the extreme reactivity of trimethyl aluminum and triethyl aluminum with water. The most reactive is trimethyl aluminum ("TMA") and accordingly the most preferred embodiment is the application of the process to make methylaluminoxane.

Any inert solvent can be used. The preferred solvents are aliphatic and aromatic hydrocarbons. Aromatic hydrocarbons are more preferred such as toluene, xylene, ethylbenzene, cumene, mesitylene and the like. The most preferred solvent is toluene.

The concentration of the hydrocarbyl aluminum compound in the inert solvent can range from about 1-30 weight percent. A preferred concentration is about 5-20 weight percent, more preferably 10-15 weight percent.

Aluminum alkyl compounds are very reactive with oxygen and compounds having active hydrogen atoms so the aluminum alkyls should be maintained under an inert gas such as nitrogen, argon, neon, methane, ethane and the like.

The amount of water emulsified in the inert solvent can range from about 0.5 to 10 weight percent. A preferred amount is about 1-3 weight percent water.

Operation of the process is best understood by reference to the drawing. In this embodiment the alkyl aluminum compound is TMA, the inert solvent is toluene and the desired product is methylaluminoxane ("MAO"). It should be understood that other aluminum alkyls and inert solvents can be substituted for the TMA and toluene.

A 5 weight percent solution of TMA in toluene is fed through conduit 1 into first reaction vessel 2 at a rate of 50 liters/minute. Toluene is fed through conduit 3 to static mixer 4. Static mixers are well-known chemical processing units and contain a plurality of vanes which divert the passing liquid through a tortuous path forming an emulsion. One source of such equipment is Koch Engineering Co., Inc., Houston, Tex. Water is metered into the toluene via conduit 5 at a rate to form a 1 weight percent water mixture. The water/toluene mixture is pumped at a rate of 60 l/min through static mixer 4 at a high velocity to form a water/toluene emulsion. The water/toluene emulsion is conducted via conduit 11 to first reaction vessel 2. Reaction vessel 2 is vigorously agitated by stirrer 12 to maintain the emulsion. Reaction vessel 2 is cooled via pump-around loop 13 passing through cooler 15. The temperature in first reaction vessel 2 was maintained at 15°–20° C.

Liquid reaction mixture is allowed to overflow through conduit 16 to second reaction vessel 17. The liquid volume in first reaction vessel 2 is 750 liters such that the average residence time was 6.8 minutes.

Second reaction vessel 17 functions to provide an additional reaction time in the absence of fresh TMA and water feed. Second reaction vessel 17 is not essential to the operation of the continuous process. It can be omitted and the reaction mixture from conduit 16 used to prepare suitable polymerization catalysts. Optionally the reaction mixture from conduit 16 can be fed to a distillation column to distill overhead part of the solvent and unreacted TMA to form a MAO concentrate. Preferably, reaction mixture from conduit 16 is held in second reaction vessel 17 for an additional reaction time and then transferred via conduit 20 to a distillation column to remove excess toluene and any unreacted TMA.

In order to have continuous operation the rate of product removal from second reactor 17 is equal to the feed rate to second reactor 17 so the reactor level remains constant. Second reactor 17 is sized to provide an average residence time of about 1–60 minutes. The temperature in second reactor 17 is about 10°–50° C.

Before proceeding with a description of specific examples, the test used to evaluate the product will be described. MAO products made by various processes result in polymerization co-catalysts of different activity even though chemical analysis of the various products is very similar. This appears to be because of the different polymeric structures and molecular weights possible with MAO. Since the prime use of aluminoxanes is as a co-catalyst with a transitional metal compound in the polymerization of olefins, a measure of this property is the most important attribute of the aluminoxane.

The activity test used by applicants involves the preparation of a catalyst complex and the use of this complex in an actual polymerization. The test procedure is similar to the process described in Ishihara et al., U.S. Pat. No. 4,680,353, incorporated herein by reference. It involves the use of a titanium compound, e.g. titanium tetraethoxide, and an alkylaluminoxane, e.g. MAO, in the polymerization of styrene to form syndiotactic polystyrene. The activity of the MAO co-catalyst is based on the grams of syndiotactic polystyrene produced in the test.

A series of reactions was conducted to prepare MAO solution. In these tests TMA/toluene solution and 1 weight percent water/toluene emulsion was fed to a reaction vessel below the liquid level while stirring the mixture vigorously. The water/toluene emulsion was pre-formed by Ultra Eurex high speed agitator followed by a static mixer. The working volume of the reactor was 750 ml. The overflow was transferred to a 2 liter distillation flask in which part of the toluene and unreacted TMA were distilled out. The following table gives the variable conditions in each example.

|  | Example |  |  |  |  |
|---|---|---|---|---|---|
|  | 1 | 2 | 3 | 4 | 5 |
| TMA/Toluene Feed |  |  |  |  |  |
| wt % TMA | 5 | 9.8 | 9.8 | 20 | 20 |
| rate (ml/min) | 50 | 60 | 80 | 25 | 50 |
| temp (°C.) | 10–15 |  |  |  |  |
| Water Emulsion Feed |  |  |  |  |  |
| rate (ml/min) | 60 | 100 | 100 | 100 | 130 |
| temp (°C.) | 25 |  |  |  |  |
| Total MAO Solution |  |  |  |  |  |
| Before Distillation (g) | 1052 | 1220 | 1280 | 1430 | 1450 |
| After Distillation (g) | 385 | 815 | 793 | 804 | 803 |
| TMA/Water Mole Ratio |  | 3.6 | 2.23 | 1.55 | 1.1 |
| Activity | 9.8 | 8.1 | 12.5 | 22.6 | 15.2 |

These tests show that the process provides a continuous process of preparing alkylaluminoxane catalyst having high activity.

I claim:

1. A continuous process for making an alkylaluminoxane, said process comprising:
   (A) feeding a solution of an alkyl aluminum compound in an inert hydrocarbon solvent to a first reaction zone,
   (B) forming an emulsion of 0.5–10 weight percent water in an inert solvent and feeding said emulsion to said first reaction zone, the ratio of moles of water to aluminum atoms being about 0.4–1:1,
   (C) removing reaction mixture from said first reaction zone at a rate that maintains a constant liquid volume in said first reaction zone, further characterized in that the combined feed rate of said solution of an alkyl aluminum compound and said emulsion results in an average residence time in said first reaction zone of about 1 to 60 minutes.

2. A process of claim 1 wherein said first stirred reaction zone is maintained at a temperature of $-20°$ C. to $30°$ C.

3. A process of claim 2 wherein said average residence time is about 1–10 minutes.

4. A process of claim 3 wherein said aluminum alkyl is a tri-$C_{1-4}$ alkyl aluminum.

5. A process of claim 4 wherein said inert solvent is an aliphatic or aromatic hydrocarbon.

6. A process of claim 5 wherein said tri-$C_{1-4}$ alkyl aluminum is trimethyl aluminum.

7. A process of claim 6 wherein said inert solvent is toluene.

8. A process of claim 5 wherein said solution of an alkyl aluminum compound contains about 1–30 weight percent of said tri-$C_{1-4}$ alkyl aluminum.

9. A process of claim 8 wherein said tri-$C_{1-4}$ alkyl aluminum is trimethyl aluminum.

10. A process of claim 9 wherein said inert solvent is toluene.

11. A process of claim 1 further characterized by including:
   (D) transferring said reaction mixture to a second reaction zone at 10°–50° C.,
   (E) removing said reaction mixture from said second reaction zone at a rate that maintains a constant liquid volume in said second reaction zone, the volume of said second reaction zone being sufficient to provide an average residence time of about 1-60 minutes.

12. A process of claim 11 wherein said aluminum alkyl is a tri-$C_{1-4}$ alkyl aluminum.

13. A process of claim 12 wherein said inert solvent is an aliphatic or aromatic hydrocarbon.

14. A process of claim 13 wherein said tri-$C_{1-4}$ alkyl aluminum is trimethyl aluminum.

15. A process of claim 14 wherein said inert solvent is toluene.

16. A process of claim 12 wherein said solution of a alkyl aluminum compound contains about 1-30 weight percent of said tri-$C_{1-4}$ alkyl aluminum.

17. A process of claim 16 wherein said tri-$C_{1-4}$ alkyl aluminum is trimethyl aluminum.

18. A process of claim 17 wherein said inert solvent is toluene.

* * * * *